United States Patent
Rivers et al.

(10) Patent No.: US 11,589,219 B2
(45) Date of Patent: Feb. 21, 2023

(54) ANONYMOUS VERIFICATION PROCESS FOR EXPOSURE NOTIFICATION IN MOBILE APPLICATIONS

(71) Applicant: THE UAB RESEARCH FOUNDATION, Birmingham, AL (US)

(72) Inventors: Claude B. Rivers, Birmingham, AL (US); Rajesh B. Pillai, Birmingham, AL (US); Zekai Demirezen, Birmingham, AL (US); Jaret A. Langston, Birmingham, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 17/403,216

(22) Filed: Aug. 16, 2021

(65) Prior Publication Data
US 2022/0053324 A1    Feb. 17, 2022

Related U.S. Application Data

(60) Provisional application No. 63/066,303, filed on Aug. 16, 2020.

(51) Int. Cl.
*H04W 12/033* (2021.01)
*G16H 50/80* (2018.01)
(Continued)

(52) U.S. Cl.
CPC .......... *H04W 12/033* (2021.01); *G16H 50/80* (2018.01); *H04W 12/068* (2021.01);
(Continued)

(58) Field of Classification Search
CPC .......... H04L 9/3236; H04W 12/068; H04W 12/069; H04W 12/69; H04W 12/06;
(Continued)

(56) References Cited

U.S. PATENT DOCUMENTS

| 7,543,149 B2 * | 6/2009 | Ricciardi | G16H 50/30 |
| | | | 713/180 |
| 8,949,940 B1 * | 2/2015 | Shenoy | G06Q 10/10 |
| | | | 707/636 |

(Continued)

FOREIGN PATENT DOCUMENTS

WO   WO-2021212113 A1 * 10/2021 ............. G06F 21/31

OTHER PUBLICATIONS

NPL: Pai et al.. "COVID-19 and your smartphone: BLE-based smart contact tracing." IEEE Systems Journal 15.4 (2021): 5367-5378.*

(Continued)

*Primary Examiner* — Lizbeth Torres-Diaz
(74) *Attorney, Agent, or Firm* — Kilpatrick Townsend & Stockton LLP

(57) ABSTRACT

The present disclosure relates exposure notification, and in particular to techniques for verification of positive test results from public health authorities where individuals submit notice using public health approved mobile applications for exposure notification and/or contact tracing. When an individual attempts to submit a positive test result notification in a mobile application, the associated device's mobile number will be requested. This mobile number will then be sent a verification code to be entered in the application. At this point, these codes shall be stored digitally in escrow. A regular data feed from a health authority shall be provided that shall include an agreed encryption (irreversibly encrypted or reversibly encrypted) of the mobile numbers associated with any reported test. Any results submitted in the application that have a matching encryption of the mobile numbers shall be released from the escrow for subsequent notification.

20 Claims, 8 Drawing Sheets

(51) Int. Cl.
*H04W 12/106* (2021.01)
*H04W 12/06* (2021.01)
*H04W 12/108* (2021.01)
*H04W 12/69* (2021.01)

(52) U.S. Cl.
CPC ....... *H04W 12/106* (2021.01); *H04W 12/108* (2021.01); *H04W 12/69* (2021.01)

(58) Field of Classification Search
CPC ... H04W 4/029; H04W 12/02; H04W 12/106; H04W 12/108; G06F 21/6245
See application file for complete search history.

(56) References Cited

U.S. PATENT DOCUMENTS

| | | | | |
|---|---|---|---|---|
| 10,033,719 | B1* | 7/2018 | Baranowski | H04L 63/123 |
| 10,617,729 | B2* | 4/2020 | Dobbins | C12Q 1/6897 |
| 2004/0064704 | A1* | 4/2004 | Rahman | G06F 16/51 |
| | | | | 707/E17.031 |
| 2004/0215981 | A1* | 10/2004 | Ricciardi | H04L 9/3236 |
| | | | | 713/176 |
| 2009/0249076 | A1* | 10/2009 | Reed | H04L 9/3228 |
| | | | | 713/168 |
| 2015/0082026 | A1* | 3/2015 | Gupta | H04L 67/10 |
| | | | | 713/155 |
| 2017/0209102 | A1* | 7/2017 | Parthasarathy | A61B 5/0059 |
| 2018/0052970 | A1* | 2/2018 | Boss | G06F 21/35 |
| 2018/0196960 | A1* | 7/2018 | Gullicksen | H04L 63/107 |
| 2018/0227128 | A1* | 8/2018 | Church | H04L 9/3247 |
| 2020/0302452 | A1* | 9/2020 | Platt | H04L 65/403 |
| 2021/0319863 | A1* | 10/2021 | Rajagopal | G06F 21/32 |
| 2022/0014357 | A1* | 1/2022 | Jones | H04L 9/0643 |
| 2022/0051808 | A1* | 2/2022 | Miettinen | G16H 40/40 |

OTHER PUBLICATIONS

NPL:Paietal.."COVID-19andyoursmartohone:BLE-basedsmartcontact-tracing." IEEESystemsJournal15.4(2021):5367-5378.*

NPL:Ahmed et al."A survey of COVID-19 contact tracing apps." IEEE access 8 (2020):134577-134601.*

"Exposure Notification, Implement a COVID-19 exposure notification system that protects user privacy", Apple Developer Documentation, retrieved at https://developer.apple.com/documentation/exposurenotification, known as early as Mar. 29, 2022.

"Exposure Notification Privacy-preserving Analytics (ENPA) White Paper", Apple and Google, retrieved at https://covid19-static.cdn-apple.com/applications/covid19/current/static/contact-tracing/pdf/ENPA_White_Paper.pdf, Apr. 2021.

* cited by examiner

ANONYMOUS VERIFICATION PROCESS FOR EXPOSURE NOTIFICATION IN MOBILE APPLICATIONS

CROSS-REFERENCE TO RELATED APPLICATION

The present application claims the benefit and priority of U.S. Provisional Patent Application No. 63/066,303, filed on Aug. 16, 2020, which is hereby incorporated by reference in its entirety for all purposes.

FIELD

The present disclosure relates to exposure notification, and in particular to techniques for identifying a subject that has tested positive for an infectious disease and notifying individuals that may subsequently have been exposed to the disease through contact (e.g., physical and/or proximal) with the subject, while maintaining privacy of the subject and individuals.

BACKGROUND

Conventional contact tracing is a technique used by public health authorities to measure and slow the spread of infectious diseases. Contact tracing slows the spread of infectious diseases by identifying potentially exposed (and therefore potentially infected) individuals, notifying the individuals that they may have been exposed to the infectious disease, helping individuals who may have been exposed get tested to confirm exposure to the infectious disease, and helping individuals who may have been exposed take appropriate action to protect their health and prevent further transmission of the infectious disease such as self-quarantine. Contact tracing typically requires manually gathering information from infected individuals about the individuals they have previously been in contact with over a set period of time (e.g., in the past week). These individuals can then be notified by public health authorities to take appropriate safety measures, such as undertaking self-quarantine and getting tested to break the chain of transmission.

SUMMARY

Embodiments are directed to providing an automated, anonymous, and asynchronous technique for verifying an identity of a subject with an infectious disease in order to notify all individuals that have recently been in contact with the subject that the individuals may have also been exposed to the disease.

In some embodiments, a method is provided that includes: receiving, by a server computer, a user identifier from a mobile application on a mobile device operated by a user, where the user identifier is provided by the user to the mobile application in response to a user receiving a test result for an infectious disease; applying, by the server computer, a first encryption function to the user identifier to generate a first encrypted output of the use identifier; storing, by the server computer, the first encrypted output of the use identifier in a data storage device; transmitting, by the server computer, a user authentication request to a device of the user using the user identifier; receiving, by the server computer, a user authentication response and contact data from the mobile application, where the contact data is collected by the mobile application during contact interactions between the mobile device and one or more other mobile devices; validating, by the server computer, the user authentication response based on the user authentication request; upon validation of the user authentication response, storing, by the server computer, the contact data in association with the first encrypted output of the use identifier in the data storage device; receiving, by the server computer, a data request message comprising a second encrypted output of the use identifier from a third-party computing device; comparing, by the server computer, the first encrypted output of the use identifier to the second encrypted output of the use identifier to determine whether the first encrypted output of the use identifier matches the second encrypted output of the use identifier; responsive to a match, retrieving, by the server computer, the contact data stored in associated with the first encrypted output of the use identifier; and transmitting, by the server computer, a data response message comprising the contact data to the third party computing device.

In some embodiments, the first encryption function is a one-way hash function or a cryptographically reversible cipher, In some embodiments, the user identifier is a phone number of the device of the user.

In some embodiments, the device of the user is the mobile device.

In some embodiments, the device of the user is a different device than the mobile device.

In some embodiments, the user authentication request is a one-time password and the user authentication response is the one-time password.

In some embodiments, the method further comprises discarding, by the server computer, the user identifier.

In some embodiments, the method further comprises receiving, by the server computer, a first encrypted output of contact data from the mobile application on the mobile device operated by the user; storing, by the server computer, the first encrypted output of the contact data in association with the first encrypted output of the use identifier in the data storage device; validating, by the server computer, the contact data based on the first encrypted output of the contact data; and upon validation of the user authentication response and the contact data, storing, by the server computer, the contact data in association with the first encrypted output of the use identifier in the data storage device.

In some embodiments, the validating comprises: comparing the user authentication response to the user authentication request; applying a second encryption function to the contact data to generate a second encrypted output of the contact data; and comparing the second encrypted output of the contact data to the first encrypted output of the contact data.

In some embodiments, the second encryption function is a one-way hash function or a cryptographically reversible cipher.

In some embodiments, the first encrypted output of the contact data is generate by the mobile application applying the second encryption function to the contact data to generate the first encrypted output of the contact data.

In some embodiments, the second encrypted output of the user identifier is generate by the third party computing device applying the first encryption function to the user identifier to generate the second encrypted output of the user identifier.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

DETAILED DESCRIPTION

I. Overview

Figure 1:
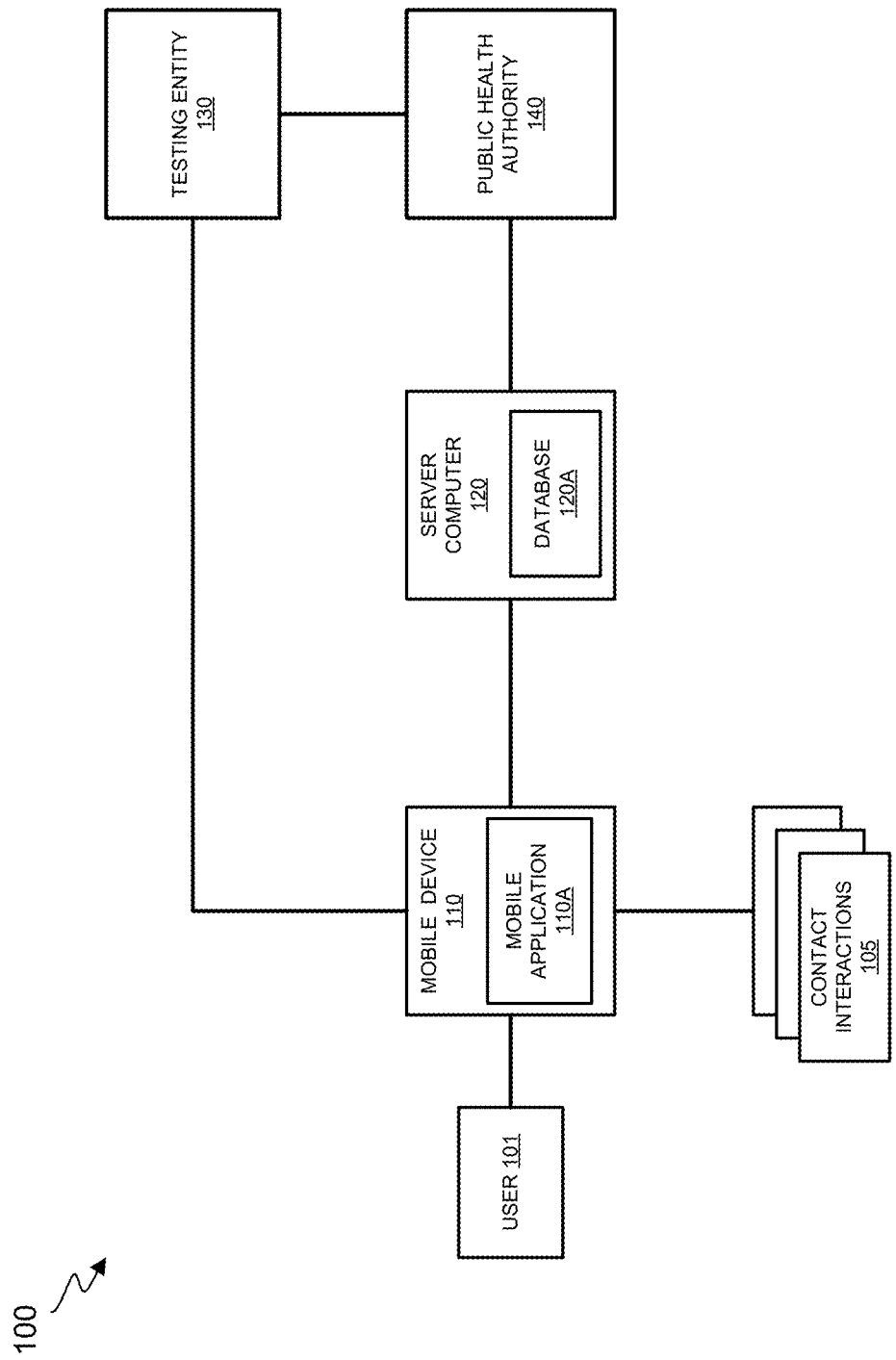
FIG. 1 shows an exemplary interaction system for collecting data and providing the collected data to a public health authority in accordance with various embodiments.

The present disclosure describes techniques for identifying a subject that has tested positive for an infectious disease and notifying individuals that may subsequently have been exposed to the disease through contact (e.g., physical and/or proximal) with the subject, while maintaining privacy of the subject and individuals. Techniques involve using, by a mobile device, a mobile notification application that includes at least a unique application identifier and wireless functionality for communicating with additional mobile notification applications on other mobile devices.

Contact tracing typically requires manually gathering information from infected individuals about the individuals they have previously been in contact with over a set period of time (e.g., in the past week). These individuals can then be notified by public health authorities to take appropriate safety measures, such as undertaking self-quarantine and getting tested to break the chain of transmission. However, there is a significant organizational burden from the conventional manual contact tracing, as many public health workers are needed to perform these tasks. Moreover, manual contact tracing can be a slow process as it requires finding and interviewing infected individuals and then reaching out and talking to their high risk contacts—all of whom may not be able to remember or know all of the people that they came in contact with in the past days to weeks. In order to overcome some of these challenges with manual contact tracing, mobile device technology has been leveraged to help identify and notify individuals who may have been exposed the infectious disease. Nonetheless, many users are reluctant to use such mobile device technology due to privacy concerns.

To address these limitations and problems, the techniques for automated exposure notification of the present embodiments implement verification of positive test results from public health authorities where individuals submit notice using public health approved mobile applications for exposure notification and/or contact tracing. When an individual attempts to submit a positive test result notification in a mobile application, the associated device's mobile number will be requested. This mobile number will then be sent a verification code to be entered in the application. At this point, these codes shall be stored digitally in escrow. A regular data feed from a health authority shall be provided that shall include an agreed encryption (irreversibly encrypted or reversibly encrypted) of the mobile numbers associated with any reported test. Any results submitted in the application that have a matching encryption of the mobile numbers shall be released from the escrow for subsequent notification.

One illustrative embodiment of the present disclosure is directed to a method that includes: receiving, by a server computer, a user identifier from a mobile application on a mobile device operated by a user, where the user identifier is provided by the user to the mobile application in response to a user receiving a test result for an infectious disease; applying, by the server computer, a first encryption function to the user identifier to generate a first encrypted output of the use identifier; storing, by the server computer, the first encrypted output of the use identifier in a data storage device; transmitting, by the server computer, a user authentication request to a device of the user using the user identifier; receiving, by the server computer, a user authentication response and contact data from the mobile application, where the contact data is collected by the mobile application during contact interactions between the mobile device and one or more other mobile devices; validating, by the server computer, the user authentication response based on the user authentication request; upon validation of the user authentication response, storing, by the server computer, the contact data in association with the first encrypted output of the use identifier in the data storage device; receiving, by the server computer, a data request message comprising a second encrypted output of the use identifier from a third-party computing device; comparing, by the server computer, the first encrypted output of the use identifier to the second encrypted output of the use identifier to determine whether the first encrypted output of the use identifier matches the second encrypted output of the use identifier; responsive to a match, retrieving, by the server computer, the contact data stored in associated with the first encrypted output of the use identifier; and transmitting, by the server computer, a data response message comprising the contact data to the third party computing device.

II. Exemplary System

FIG. 1 shows an exemplary interaction system 100 for collecting and distributing data relevant to anonymously maintaining a record of disease exposure.

As shown in FIG. 1, system 100 may include a mobile device 110 operated by a user 101. Mobile device 110 may be a mobile phone, a tablet computer, a PDA, a wearable device, and/or any other suitable device that may be transported and operated by user 101. Mobile device 110 may further include Bluetooth, Bluetooth Low Energy (BLE), and/or the like technologies with short-wave length wireless capability for short distance communication with other mobile devices. Mobile device 110 includes at least a mobile application 110A (e.g., a mobile notification application), which is configured to collected, maintain, and release a record of individuals that the user 101 has been in contact. Mobile application 110A establishes the record of each individual using a unique application identifier, which is a code or string of alphanumeric characters, that is randomly generated by the mobile application 110A during a user registration of the mobile application 110A.

Contact interactions 105 occur between individuals when the mobile device 110 operated by user 101 is within a wireless communication range (e.g., Bluetooth) of one or more other mobile devices having the same mobile application 110A over an uninterrupted period of time (e.g., such as 10 minutes, 15 minutes, etc.). In some instances, the mobile device 110 is within a proximity of the one or more other mobile devices for at least 15 minutes or longer in order to initiate a contact interaction 105. Therefore, individuals within a defined proximity of mobile device 110 for a period greater than the allotted time period (e.g., in this case, less than 15 minutes) will be determined as having a contact interaction 105 with the user 101 of the mobile device 110. Whereas, individuals outside the defined proximity of the mobile device 110 or within the defined proximity of mobile device 110 for a period less than the allotted time period (e.g., in this case, less than 15 minutes) will be determined as not having a contact interaction 105 with the user 101 of the mobile device 110. In certain instances, the proximity is defined by the physical range of the wireless communication (typically less than 10 m (33 ft) for Bluetooth).

Each determined contact interaction 105 triggers the mobile application 110A of the mobile device 110 to transmit the application identifier associated with the mobile application 110A to the other mobile device determined to have the contact interaction 105 with the mobile device 110. Additionally, the mobile application 110A will receive an application identifier associated with the mobile application from the other mobile device. These received application identifiers may then be stored on the mobile notification application of each respective mobile device. For example, mobile application 110A may access one or more memory storage elements of mobile device 110 to at least store the received application identifier from the contact interaction 105. Accordingly, the mobile application 110A of each respective mobile device is capable of collecting application identifiers for each mobile application 110A that the individuals come into contact with through-out the course of each day.

In some embodiments, the user 101 may wish to get tested for presence of an infectious disease at a testing entity 130, such as a hospital, a lab, and/or any suitable testing center. The testing process may include taking a sample (e.g., a nasal swab or blood sample) from the user 101 and testing the sample for a presence of the infectious disease. During the testing process, the user 101 submits contact information (e.g., a phone number for the mobile device) to the testing entity 130 that becomes associated with the sample and a result of testing the sample. In some instances, the contact information may be submitted through the mobile device 110 and/or mobile application 110A. For example, in order to receive and/or access testing results, the mobile device 110 and/or mobile application 110A may be in communication with testing entity 130 and share information such as the contact information. Testing results may include a positive and/or negative indicator that identifies either a presence or absence of the disease for user 101. The testing entity 130 reports the testing results in association with the contact information to a third party 140, such as a public health authority, such that the third party can take action based on the testing results to reduce the spread of the infectious disease (e.g., contact tracing).

In the event that the user 101 tests positive for a presence of the infectious disease, the user 101 is given an option via the mobile application 110A to submit the application identifiers collected on the mobile device 110 over a prior period time (e.g., the past 14 days, 21 days, 30 days, etc.) to a third party 140. Submission includes the user 101 providing the mobile notification application 110A the same contact information (e.g., a phone number for the mobile device 110) that the user 101 had previously provided to the testing entity 130, which is associated with the sample and a result of testing the sample (e.g., a positive or negative test result).

Upon the user 101 choosing to submit the application identifiers collected on the mobile device 110 to the third party 140, the mobile application 110A is used to obtain contact information for the user 101 (e.g., via a graphical user interface). Additionally, the mobile application 110A may apply an encryption function to the application identifiers collected on the mobile device 110 to obtain a first encrypted output of the application identifiers such as a fixed-length binary sequence (i.e., a bit array of a fixed size). Encryption is a security control used primarily to provide confidentiality protection for data. It is a mathematical transformation to scramble data requiring protection (plaintext) into a form not easily understood by unauthorized people or machines (ciphertext). After being transformed into ciphertext, the plaintext appears random and does not reveal anything about the content of the original data. Once encrypted, no person (or machine) can discern anything about the content of the original data by reading the encrypted form of the data. In some instances, the encryption function is reversible such as application of a cryptographically reversible cipher. A reversible encryption process has a corresponding decryption process, which is used to reverse the encrypted data (ciphertext) back to its original content (plaintext). In other embodiments, the encryption function is irreversible such as application of a one-way hash function A one-way hash function is a mathematical function that generates a fingerprint of the input (e.g., the application identifiers), but there is no way to get back to the original input. If the input is the same then the hash is always the same, if it changes at all, even by one character the encrypted output is completely different. Although aspects of the present disclosure pertain to application of an encryption function, it should be understood that it is contemplated that for applications where data privacy is of little concern or no concern, the raw data (e.g., user identifier and/or application identifiers) may be used (an encryption function is not applied) without departing from the spirit and scope of the present disclosure.

The mobile application 110A sends the contact information and optionally the encrypted output to an application backend server 120. The application backend server 120 may be a cloud server computer that acts as a backend for the mobile application 110A. The backend is the code that runs on the server, that receives requests from the application 110A, and contains the logic to send the appropriate data back to the mobile application 110A. The application backend server 120 also includes a memory storage device 120A such as a database, which will persistently store all of the data for the application 110A.

The application backend server 120 receives the contact information and optionally the first encrypted output of the application identifiers, and applies an encryption function (same or different encryption function as applied by the application 110A) to the contact information to obtain a first encrypted output of the contact information. The application backend server 120 saves the first encrypted output of the application identifiers and optionally the first encrypted output of the contact information in association with one another to a data storage device 120A. Thereafter, the application backend server 120 generates a one-time password and sends the one-time password to the mobile device 110 using the contact information (e.g., phone number for the mobile device 110) for verifying the contact number and optionally the application identifiers submitted to the application backend server 120 by the mobile application 110A. A one-time password, also known as one-time pin or dynamic password, is a password that is valid for only one login session or transaction, on a computer system or other digital device. In some instances, the application backend server 120 sends the one-time password off band through short message service (SMS). The application backend server 120 then discards the contact information (i.e., deletes or removes the contact information from memory of the application backend server).

The mobile device 110 associated with the contact information receives the one-time password, and the user 101 (if same user that chose to submit the application identifiers collected on their mobile device) inputs the one-time password into the mobile application 110A on the mobile device 110. In response to receiving the input of the one-time password, the mobile application 110A sends the one-time password and the application identifiers collected on the mobile device 110 to the application backend server 120.

The application backend server 120 receives the one-time password and the application identifiers, and checks validity of the one-time password and optionally the application identifiers. The validity of the one-time password may be checked by comparing the received one-time password against the one-time password that was sent to the user 101. The validity of the application identifiers may be confirmed by applying the encryption function to the application identifiers to obtain a second encrypted output of the application identifiers and comparing the second encrypted output of the application identifiers to the first encrypted output of the application identifiers stored in the data storage device 120A. If the validity of the one-time password and/or the application identifiers cannot be confirmed then the application identifiers may be discarded (i.e., deletes or removes the application identifiers from memory of the application backend server 120). If the validity of the one-time password and/or the application identifiers can be confirmed, then the application backend server 120 saves the application identifiers submitted by the mobile device 110 to the data storage device 120A along with the associated first encrypted output of the application identifiers and the first encrypted output of the contact information.

The third party 140, upon obtaining a positive test result, applies an encryption function (same encryption function as applied by the application backend server 120 to the contact information) to the contact information associated with the positive test result to obtain a second encrypted output of the contact information. The third party 140 sends the second encrypted output of the contact information (e.g., encrypted output such as hashes of all contact information associated with all positive test results) to the application backend server 120. In some instances, the third party 140 sends the second encrypted output of the contact information asynchronously. Asynchronous communication is transmission of data, generally without the use of an external clock signal, where data can be transmitted intermittently rather than in a steady stream.

Upon receipt of the second encrypted output of the contact information from the third party 140, the application backend server 120 compares the second encrypted output of the contact information to the first encrypted outputs of the contact information stored in the memory storage device 120A. If the second encrypted output of the contact information matches one of the first encrypted outputs of the contact information, then the application backend server 120 releases and sends the application identifiers associated with the matched first encrypted output of the contact information to the third party 140.

At a later point, the third party 140 such as the public health authority and/or some other third party entity may use the application identifiers as deemed fit to help reduce the spread of the infectious disease. For example, the third party 140 can use the application identifiers to notify associated individuals that they may have been exposed to the infectious disease through contact with the user 101. The notification may be provided manually (e.g., a public health worker calling the individual) or via the mobile application 110A (e.g., a push notification to the mobile device of the individual). Notifications may further be accompanied with instructions and/or suggestions to prevent further spread of the disease. Such suggestions may include a notified individual getting tested at a testing entity to confirm a presence of the disease and/or the notified individual limiting contact with other individuals and the general public. Advantageously, these approaches are automated, anonymous and asynchronous.

III. Exemplary Methods

Figure 2:
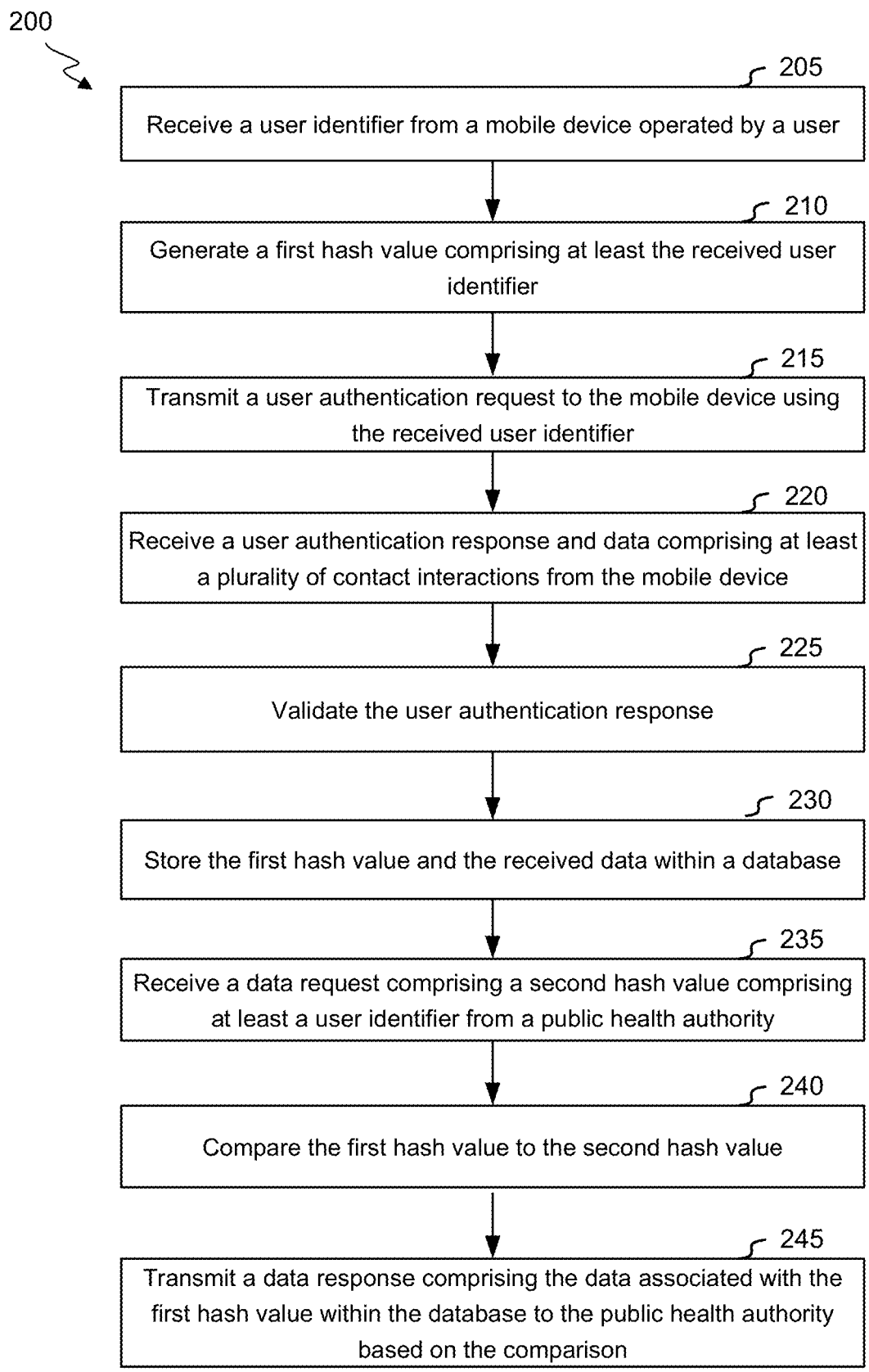
FIG. 2 shows an exemplary method for receiving and distributing health data associated with an exposed user using a server computer in accordance with various embodiments.

FIG. 2 shows a flowchart of a process 200 for receiving and transmitting contact data associated with a user that has been exposed to a disease. The process 200 depicted in FIG. 2 may be implemented in software (e.g., code, instructions, program) executed by one or more processing units (e.g., processors, cores) of the respective systems, hardware, or combinations thereof. The software may be stored on a non-transitory storage medium (e.g., on a memory device). The process 200 presented in FIG. 2 and described below is intended to be illustrative and non-limiting. Although FIG.

2 depicts the various processing steps occurring in a particular sequence or order, this is not intended to be limiting. In certain alternative embodiments, the steps may be performed in some different order or some steps may also be performed in parallel. In certain embodiments, such as in the embodiments depicted in FIG. 1, process 200 may be performed using one or more computing systems (e.g., system 100 described with respect to FIG. 1). In some embodiments, application backend server 120 is configured to perform the method of process 200.

Process 200 is initiated when a user wishes to submit his/her contact data in response to receiving a positive result for a presence of a disease from a testing entity. In such instances, a user may operate a mobile device and access a mobile notification application in communication with a server computer. The user may input a user identifier into the mobile notification application and enable a submission process.

At block 205, the user identifier is received from the mobile notification application at the server computer. In some instances, the user identifier is contact information such as a mobile phone number and/or another form of contact information (e.g., email) associated with the user that allows the server computer to contact a device of the user associated with the user identifier for user authentication. The received user identifier is a same user identifier that the user provided to the public health authority and/or a testing entity at a time of testing for the infectious disease.

Optionally, the server computer receives encrypted contact data with the user identifier. The contact data is data associated with one or more contact interactions that the user has had with other users within a recent time period (e.g., within a last week or a last 2 weeks). In some instances, the contact data is one or more application identifiers (e.g., such as unique key and/or a code) that the mobile notification application receives from one or more mobile devices belonging to the other contacted users in response to each of the contact interactions. Encrypting of the contact data may involve application of an encryption function to the contact data, which is performed by the mobile notification application prior to transmitting the contact data (e.g., a first encrypted output of contact data collected by the mobile notification application).

At block 210, the server computer applies an encryption function (same or different encryption function as applied by the mobile notification application) to the user identifier to obtain a first encrypted output of the user identifier. The server computer saves the first encrypted output of the user identifier and optionally the encrypted contact data in association with one another to a data storage structure.

At block 215, the server computer generates a one-time password and sends a user authentication request with the one-time password to the user's device using the contact information (e.g., the user's mobile device) for verifying the user identifier and optionally the contact data submitted to the server computer by the mobile notification application. The user receives the one-time password at their device and is prompted to enter the one-time password within a field of the mobile notification application. In response to receiving the input of the one-time password, the mobile notification application sends the one-time password and the contact data (unencrypted), such as the application identifiers collected on the user's mobile device, to the server computer.

At block 220, the server computer receives a user authentication response and the contact data. The user authentication response includes the one-time password.

At block 225, the server computer checks the validity of the one-time password and optionally the contact data. The server computer may validate the received user authentication response by at least comparing the received one-time password to the one-time password that the server computer initially sent to the user's device. The server computer may further validate the received contact data by comparing the received contact data to the encrypted contact data (e.g., a first encrypted output of the contact data) that was received at block 205. In some instances, the comparison includes the server computer applying a encryption function (same encryption function applied by the mobile notification application) to the received contact data to generate additional encrypted contact data (e.g., a second encrypted output of the contact data) and determining if the additional encrypted contact data matches the encrypted contact data received at block 205.

Not shown, if the validity of the one-time password and/or the contact data cannot be confirmed then the contact data is discarded (i.e., deleted or removed the contact data from memory of the application backend server).

At block 230, if the validity of the one-time password and/or the contact data can be confirmed, then the server computer saves the contact data submitted by the mobile device to the data storage device along with the encrypted contact data and the first encrypted output of the user identifier. In particular, the first encrypted output of the user identifier may be mapped to the received contact data within the data storage device to indicate that the received contact data is associated with the user.

At block 235, a data retrieval message comprising a second encrypted output of a user identifier is received from the third party. The second encrypted output of the user identifier is generated by the third party using at least a user identifier and a same encryption function as used by the server computer. The user identifier may be retrieved from the user or the testing entity by the third party at a time of testing for presence of the infectious disease.

At block 240, the first encrypted output of the user identifier is compared to the second encrypted output of the user identifier. If the first encrypted output of the user identifier and the second encrypted output of the user identifier match, the contact data associated with the first encrypted output of the user identifier is retrieved from the memory storage device using the first encrypted output of the user identifier.

At block 245, a data response message comprising the contact data collected from the one or more contact interactions is generated and transmitted to the third party by the server computer.

The public health authority may extract the collected contact data from the data response message and use the data to notify each individual associated with the plurality of contact interactions. In most instances, the contact data may be used to generate one or more push notifications that can be transmitted to a mobile notification application associated with each of the plurality of contact interactions, such that the one or more push notifications can notify each individual that has been identified as having contact with the user via the contact data that the respective individual may have been exposed to the disease.

Figure 3:
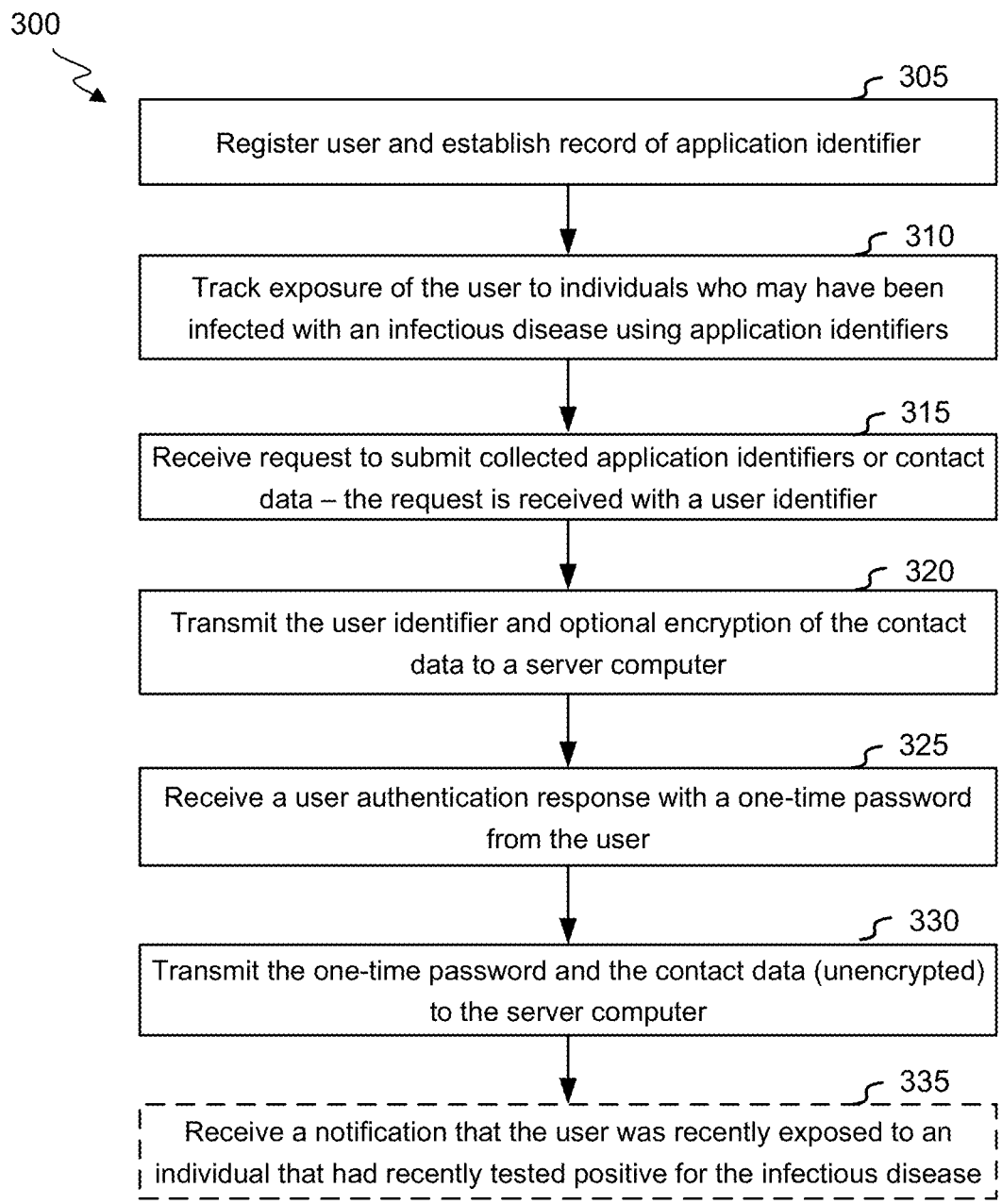
FIG. 3 shows an exemplary method for receiving and distributing health data associated with an exposed user using a mobile application in accordance with various embodiments.

FIG. 3 shows a flowchart of a process 300 for receiving and transmitting contact data associated with a user that has been exposed to an infectious disease. The process 300 depicted in FIG. 3 may be implemented in software (e.g., code, instructions, program) executed by one or more processing units (e.g., processors, cores) of the respective systems, hardware, or combinations thereof. The software may be stored on a non-transitory storage medium (e.g., on a memory device). The process 300 presented in FIG. 3 and described below is intended to be illustrative and non-limiting. Although FIG. 3 depicts the various processing steps occurring in a particular sequence or order, this is not intended to be limiting. In certain alternative embodiments, the steps may be performed in some different order or some steps may also be performed in parallel. In certain embodiments, such as in the embodiments depicted in FIG. 1, process 300 may be performed using one or more computing systems (e.g., system 100 described with respect to FIG. 1). In some embodiments, mobile application 110A is configured to perform the method of process 300.

Process 300 is initiated when a user wishes to obtain and register for using a mobile notification application for collecting and distributing data relevant to anonymously maintaining a record of disease exposure. At block 305, the user registers with the mobile notification application. The registration includes the mobile notification application establishing a record of the user using a unique application identifier, which is a code or string of alphanumeric characters, that is randomly generated by the mobile notification application.

At block 310, the mobile notification application tracks exposure of the user to individuals who may have been infected with infectious disease. Exposure to the disease may be tracked by the mobile notification application by performing an exchange of unique application identifiers with each contacted individual. The contact between individuals may be defined as the mobile device of the user being within a wireless communication range (e.g., Bluetooth) as one or more other mobile devices of one or more other users over an uninterrupted period of time (e.g., such as 10 minutes, 15 minutes, etc.). At a time of contact between the user and the one or more other users, the application identifier associated with the user may be transmitted to the one or more other mobile devices belonging to the one or more other users and the application identifier(s) associated with the one or more other users may be transmitted to the mobile device belonging to the user. These received application identifiers or contact data may then be stored by the mobile notification application of each respective mobile device.

At block 315, the user may wish to submit his/her received application identifiers or contact data in response to receiving a positive result for a presence of the infectious disease from a testing entity. In such instances, a user may operate the mobile device and access the mobile notification application in communication with a server computer. The user may input a user identifier into the mobile notification application and enable a submission process. The user identifier is received from the mobile notification application at the server computer. In some instances, the user identifier is contact information such as a mobile phone number and/or another form of contact information (e.g., email) associated with the user that allows the server computer to contact a device of the user associated with the user identifier for user authentication. The received user identifier is a same user identifier that the user provided to the public health authority and/or a testing entity at a time of testing for the infectious disease.

Optionally, the mobile notification application encrypts the received application identifiers or contact data. Encrypting of the received application identifiers or contact data may involve application of an encryption function to the received application identifiers or contact data, which is performed by the mobile notification application prior to transmitting the contact data (e.g., a first encrypted output of contact data collected by the mobile notification application).

At block 320, the mobile notification application transmits the user identifier and optionally the first encrypted output of the contact data to the server computer.

At block 325, the mobile notification application receives a user authentication response with a one-time password from the user. The user receives the one-time password at their device (same or different device as the mobile device) and is prompted to enter the one-time password within a field of the mobile notification application.

At block 330, in response to receiving the input of the one-time password, the mobile notification application sends the one-time password and the contact data (unencrypted), such as the application identifiers collected on the user's mobile device, to the server computer.

At block 335, optionally, the mobile notification application receives a notification that the user was recently exposed to an individual that has tested positive for the infectious disease. The notification may be received at any point in time after the user has registered for using the mobile notification application at block 305. The mobile notification application may specifically be configured to display recent exposure data including a date and/or time that the data was last updated. In some instances, the exposure data may include a count of recent exposures. In other instances, the exposure data may include a list of each individual possible exposure incident and a resulting date and/or time that the respective incident was reported to a public health authority.

VI. Example Use Case

FIGS. 4-8 illustrate exemplary graphical user interfaces of a mobile notification application implementing the above described techniques.

Figure 4:
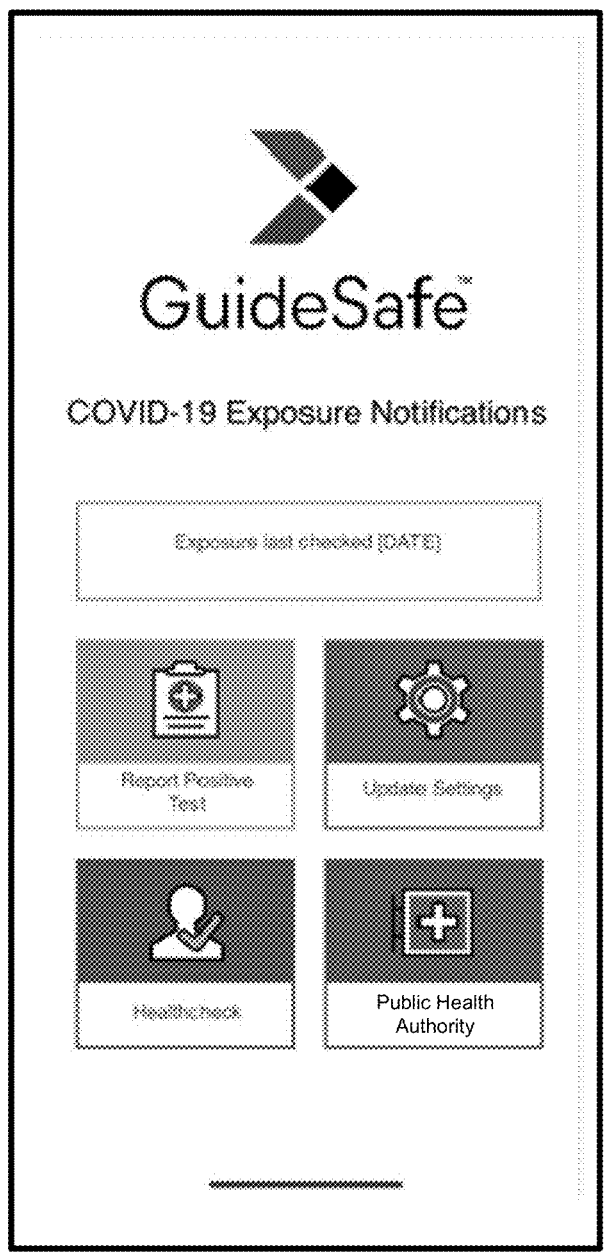
FIG. 4 shows an exemplary user interface element for the mobile application in accordance with various embodiments.
Figure 5:
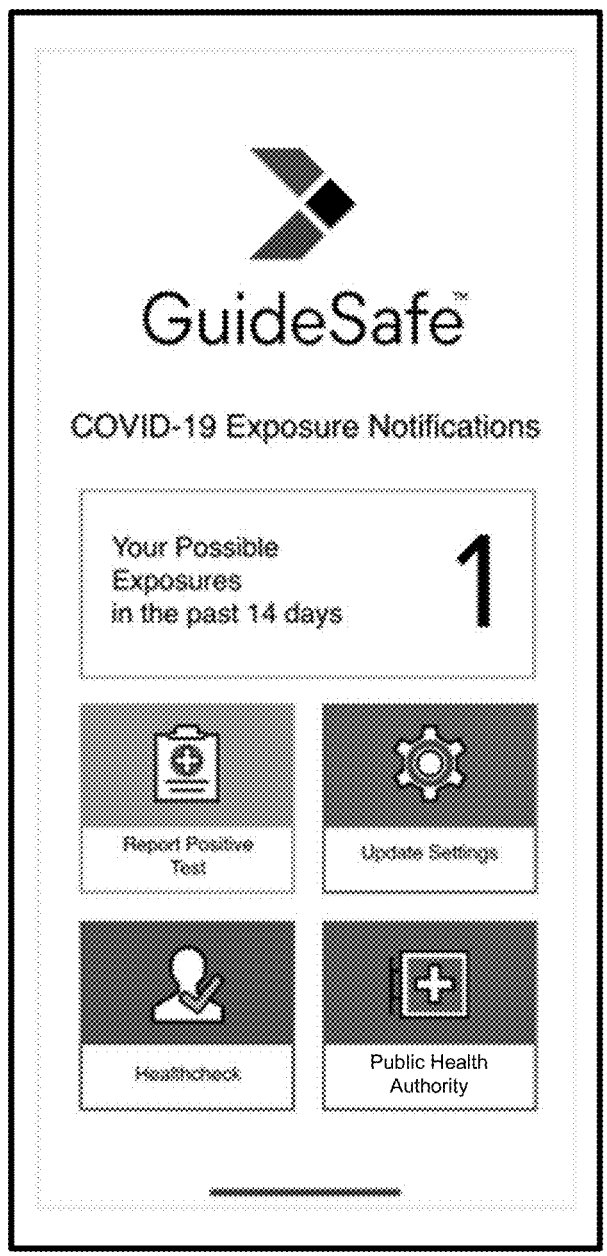
FIG. 5 shows another exemplary user interface element for the mobile application, including a notification of exposure in accordance with various embodiments.

A user may download and register with a mobile notification application that is configured to specifically manage exposure notifications for an infectious disease. Referring to FIG. 4, the mobile notification application may specifically be configured to display recent exposure data including a date and/or time that the data was last updated. In some instances, the exposure data may include a count of recent exposures as illustrated in FIG. 5. In other instances, the exposure data may include a list of each individual possible exposure incident and a resulting date and/or time that the respective incident was reported to a public health authority. The mobile notification application may additionally include an option for reporting a positive test result of the disease (e.g., in this case, COVID-19 which is an infectious disease caused by severe acute respiratory syndrome coronavirus 2 (SARS-CoV-2)). Additional options may be included for contacting a local public health authority, receiving information related to symptoms, treatment, and/or prevention of the disease, and/or getting an online assessment that prompts the user to enter current symptoms and determines whether or not the user should get a test based on the entered symptoms. The user can further configure one or more settings for the application, such as a frequency of exposure notifications.

In the event that the user receives test results indicating that he/she has the infectious disease from a testing center, the user may then decide to notify the mobile health application by selecting the option for reporting a positive test result.

Figure 6:
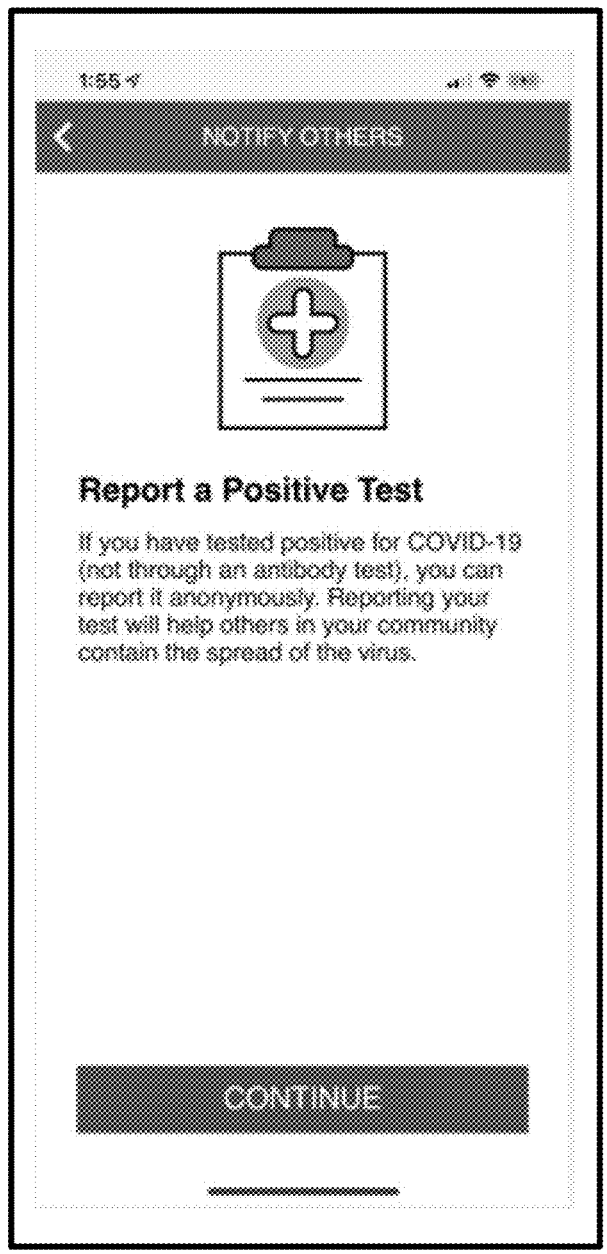
FIG. 6 shows an exemplary user interface element for the process of reporting test results using the mobile application in accordance with various embodiments.
Figure 7:
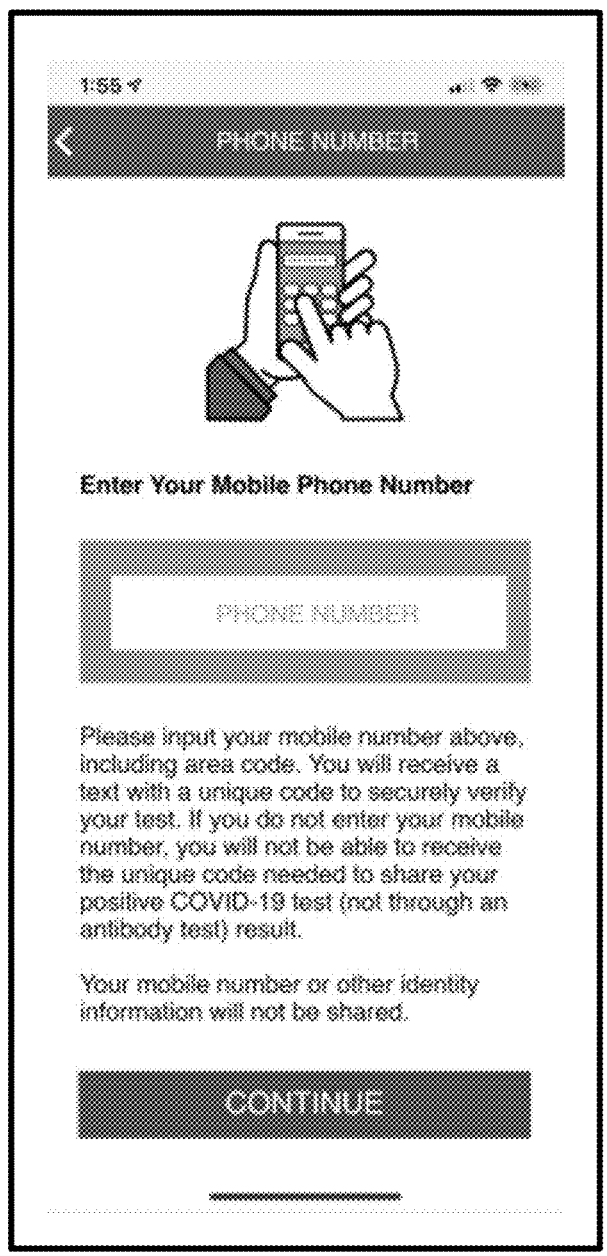
FIG. 7 shows an exemplary user interface element for providing a user identifier to a backend server computer during a process of reporting test results using the mobile application in accordance with various embodiments.
Figure 8:
FIG. 8 shows an exemplary interface for inputting a verification code during a process of reporting rest results using the mobile application in accordance with various embodiments.

FIGS. 6-8 illustrate an exemplary flow for reporting these results. As part of this flow, the user may be prompted to provide a user identifiers such as a phone number into an input data field of the mobile notification application as shown in FIG. 7.

Upon user entry, the mobile notification application may then extract the number from the data field, verify the extracted number is a valid phone number, and in conjunction with a backend server use the number to send a SMS communication to the mobile device of the user with a verification code.

The user may then enter the verification code into another input data field of the mobile notification application as shown in FIG. 8. If the verification code is valid, then the mobile notification application may transmit all stored exposure data based on the user's recent interactions and/or contact with other individuals to the backend server of the mobile notification application. The backend server may then facilitate a data transfer with a third party such as a public health authority, which will subsequently send notifications of a possible exposure to the disease to all of the individuals that have been recorded as being in contact with the user.

Embodiments of the present disclosure are particularly advantageous because they involve the use of a user identifier such as a mobile phone number as the primary user identifying information, which enables an automated and anonymous process of identifying the user while still maintaining anonymity of the user. Private user information such as a name and/or a date of birth are not provided and/or accessible to the mobile application or the backend server. Notified individuals additionally are only notified that they have potentially been exposed to the disease but do not have any way of knowing the identity of the user responsible for the possible exposure.

V. Additional Considerations

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method comprising:
   receiving, by a server computer, a user identifier from a mobile application on a mobile device operated by a user, wherein the user identifier is provided by the user to the mobile application in response to a user receiving a test result for an infectious disease;
   applying, by the server computer, a first encryption function to the user identifier to generate a first encrypted output of the user identifier;
   storing, by the server computer, the first encrypted output of the user identifier in a data storage device;

transmitting, by the server computer, a user authentication request to a device of the user using the user identifier;
receiving, by the server computer, a user authentication response and contact data from the mobile application, wherein the contact data is collected by the mobile application during contact interactions between the mobile device and one or more other mobile devices;
validating, by the server computer, the user authentication response based on the user authentication request;
upon validation of the user authentication response, storing, by the server computer, the contact data in association with the first encrypted output of the user identifier in the data storage device;
receiving, by the server computer, a data request message comprising a second encrypted output of the user identifier from a third-party computing device;
comparing, by the server computer, the first encrypted output of the user identifier to the second encrypted output of the user identifier to determine whether the first encrypted output of the user identifier matches the second encrypted output of the user identifier;
responsive to a match, retrieving, by the server computer, the contact data stored in association with the first encrypted output of the user identifier; and
transmitting, by the server computer, a data response message comprising the contact data to the third-party computing device.

2. The method of claim 1, wherein the user identifier is a phone number of the device of the user.

3. The method of claim 1, wherein the device of the user is the mobile device.

4. The method of claim 1, wherein the device of the user is a different device than the mobile device.

5. The method of claim 1, wherein the user authentication request is a one-time password.

6. The method of claim 5, wherein the user authentication response is the one-time password.

7. The method of claim 1, further comprising discarding, by the server computer, the user identifier.

8. The method of claim 1, further comprising:
receiving, by the server computer, a first encrypted output of contact data from the mobile application on the mobile device operated by the user;
storing, by the server computer, the first encrypted output of the contact data in association with the first encrypted output of the user identifier in the data storage device;
validating, by the server computer, the contact data based on the first encrypted output of the contact data; and
upon validation of the user authentication response and the contact data, storing, by the server computer, the contact data in association with the first encrypted output of the user identifier in the data storage device.

9. The method of claim 8, wherein the validating comprises:
comparing the user authentication response to the user authentication request;
applying a second encryption function to the contact data to generate a second encrypted output of the contact data; and
comparing the second encrypted output of the contact data to the first encrypted output of the contact data.

10. The method of claim 9, wherein the first encrypted output of the contact data is generate by the mobile application applying the second encryption function to the contact data to generate the first encrypted output of the contact data.

11. The method of claim 9, wherein the second encrypted output of the user identifier is generated by the third-party computing device applying the first encryption function to the user identifier to generate the second encrypted output of the user identifier.

12. The method of claim 9, wherein the first encryption function is a one-way hash function or a cryptographically reversible cipher.

13. The method of claim 9, wherein the second encryption function is a one-way hash function or a cryptographically reversible cipher.

14. A system comprising:
one or more data processors; and
a non-transitory computer readable storage medium containing instructions which, when executed on the one or more data processors, cause the one or more data processors to perform actions including:
receiving a user identifier from a mobile application on a mobile device operated by a user, wherein the user identifier is provided by the user to the mobile application in response to a user receiving a test result for an infectious disease;
applying a first encryption function to the user identifier to generate a first encrypted output of the user identifier;
storing the first encrypted output of the user identifier in a data storage device;
transmitting a user authentication request to a device of the user using the user identifier;
receiving a user authentication response and contact data from the mobile application, wherein the contact data is collected by the mobile application during contact interactions between the mobile device and one or more other mobile devices;
validating the user authentication response based on the user authentication request;
upon validation of the user authentication response, storing the contact data in association with the first encrypted output of the user identifier in the data storage device;
receiving a data request message comprising a second encrypted output of the user identifier from a third-party computing device;
comparing the first encrypted output of the user identifier to the second encrypted output of the user identifier to determine whether the first encrypted output of the user identifier matches the second encrypted output of the user identifier;
responsive to a match, retrieving the contact data stored in association with the first encrypted output of the user identifier; and
transmitting a data response message comprising the contact data to the third-party computing device.

15. The system of claim 14, wherein the actions further include:
receiving a first encrypted output of contact data from the mobile application on the mobile device operated by the user;
storing the first encrypted output of the contact data in association with the first encrypted output of the user identifier in the data storage device;
validating the contact data based on the first encrypted output of the contact data; and
upon validation of the user authentication response and the contact data, storing the contact data in association with the first encrypted output of the user identifier in the data storage device.

16. The system of claim 15, wherein the validating comprises:
- comparing the user authentication response to the user authentication request;
- applying a second encryption function to the contact data to generate a second encrypted output of the contact data; and
- comparing the second encrypted output of the contact data to the first encrypted output of the contact data.

17. The system of claim 16, wherein the first encrypted output of the contact data is generated by the mobile application applying the second encryption function to the contact data to generate the first encrypted output of the contact data.

18. A non-transitory machine-readable storage medium, including instructions configured to cause one or more data processors to perform actions including:
- receiving a user identifier from a mobile application on a mobile device operated by a user, wherein the user identifier is provided by the user to the mobile application in response to a user receiving a test result for an infectious disease;
- applying a first encryption function to the user identifier to generate a first encrypted output of the user identifier;
- storing the first encrypted output of the user identifier in a data storage device;
- transmitting a user authentication request to a device of the user using the user identifier;
- receiving a user authentication response and contact data from the mobile application, wherein the contact data is collected by the mobile application during contact interactions between the mobile device and one or more other mobile devices;
  - validating the user authentication response based on the user authentication request;
  - upon validation of the user authentication response, storing the contact data in association with the first encrypted output of the user identifier in the data storage device;
- receiving a data request message comprising a second encrypted output of the user identifier from a third-party computing device;
- comparing the first encrypted output of the user identifier to the second encrypted output of the user identifier to determine whether the first encrypted output of the user identifier matches the second encrypted output of the user identifier;
- responsive to a match, retrieving the contact data stored in association with the first encrypted output of the user identifier; and
- transmitting a data response message comprising the contact data to the third-party computing device.

19. The non-transitory machine-readable storage medium of claim 18, wherein the actions further include:
- receiving a first encrypted output of contact data from the mobile application on the mobile device operated by the user;
- storing the first encrypted output of the contact data in association with the first encrypted output of the user identifier in the data storage device;
- validating the contact data based on the first encrypted output of the contact data; and
- upon validation of the user authentication response and the contact data, storing the contact data in association with the first encrypted output of the user identifier in the data storage device.

20. The non-transitory machine-readable storage medium of claim 19, wherein the validating comprises:
- comparing the user authentication response to the user authentication request;
- applying a second encryption function to the contact data to generate a second encrypted output of the contact data; and
- comparing the second encrypted output of the contact data to the first encrypted output of the contact data.

* * * * *